US007745167B2

(12) United States Patent
Harner et al.

(10) Patent No.: US 7,745,167 B2
(45) Date of Patent: Jun. 29, 2010

(54) FIBER-OPTIC PROBES AND METHODS OF MEASURING BIOLOGICAL MATERIALS

(75) Inventors: Richard S. Harner, Midland, MI (US); Timm R. Richardson, Midland, MI (US); Keith L. Haney, San Diego, CA (US); Torben R. Bruck, La Mesa, CA (US); Lawrence C. Chew, San Diego, CA (US)

(73) Assignee: Dow Global Technologies, Inc., Midland, MI (US)

( * ) Notice: Subject to any disclaimer, the term of this patent is extended or adjusted under 35 U.S.C. 154(b) by 298 days.

(21) Appl. No.: 11/528,872

(22) Filed: Sep. 28, 2006

(65) Prior Publication Data

US 2007/0081759 A1    Apr. 12, 2007

Related U.S. Application Data

(60) Provisional application No. 60/721,684, filed on Sep. 29, 2005.

(51) Int. Cl.
*C12N 1/00* (2006.01)
*C12Q 1/02* (2006.01)
*G02B 6/00* (2006.01)
*C02F 1/00* (2006.01)
*G01N 21/00* (2006.01)

(52) U.S. Cl. ............ 435/29; 385/12; 210/745; 356/441; 435/243

(58) Field of Classification Search ............ None
See application file for complete search history.

(56) References Cited

U.S. PATENT DOCUMENTS 4,707,134 A  *  11/1987  McLachlan et al. ......... 356/342

6,054,262 A  *  4/2000  Hayakawa et al. ............. 435/4

OTHER PUBLICATIONS

Robrish et al. Use of a Fiber Optic Probe for Spectral Measurements and the Continuous Recording of the Turbidity of Growing Microbial Cultures; Applied Microbiology, vol. 21, No. 2 (1971) pp. 278-287.*
Evaluation and Applications of Optical Dell Density Probes in Mammalian Cell Bioreactors, Wu, P., et al., Biotechnology and Bioengineering, vol. 45, pp. 495-502 (1995), John Wiley and Sons.
The Effects of Aeration and Agitation on the Measurement of Yeast Biomass Using a Laser Turbidity Probe, Gregory, E., et al., Bioprocessing Engineering, 16, (1997), 339-344, Springer-Verlag.
A Novel Optical Fibre Sensor for Turbidity Measurement, F. H. Zhang, et al., Electrical Electronic engineering and Physics, (1996) pp. 370-373 Liverpool John Moores University, Liverpool, UK.

* cited by examiner

*Primary Examiner*—Rebecca E. Prouty
*Assistant Examiner*—Paul C. Martin
(74) *Attorney, Agent, or Firm*—Jarett Abramson

(57) ABSTRACT

A method for monitoring fluid media, such as a dynamic biological system, in a biological reactor containing developing culture fluid media. The method includes the step of directing light into the fluid media by way of one or more optical fibers to produce an illuminated fluid media and then measuring the intensity of light reflected from the illuminated fluid media by way of one or more optical fibers, the optical fibers being partitioned from the fluid media by a transparent window having inner and outer surfaces; the fibers having ends terminating adjacent to and confronting the inner surface of the window and extending in a direction away from the window, the corresponding ends of the fibers being radially and circumferentially spaced from one another, the corresponding ends of the fibers having converging and intersecting longitudinal projections therefrom, the intersecting longitudinal projections from the fibers being entirely within the window. Additionally, a fiber-optic probe is discussed.

20 Claims, 5 Drawing Sheets

FIBER-OPTIC PROBES AND METHODS OF MEASURING BIOLOGICAL MATERIALS

CROSS-REFERENCE TO RELATED APPLICATION

This application claims priority to U.S. Provisional Application No. 60/721,684, filed Sep. 29, 2005, the disclosure of which is incorporated herein by reference in its entirety.

FIELD OF THE INVENTION

This invention relates to fiber-optic probes and methods for use of such optic probes to measure biological materials. More specifically, the fiber-optic probe can be utilized for the in situ measurement of biological materials to allow for measuring high optical density (OD) levels and/or biomass concentration.

BACKGROUND OF THE INVENTION

The use of bacterial cells to produce protein-based therapeutics is increasing in commercial importance. One of the goals in developing a bacterial expression system is the production of high quality target polypeptides quickly, efficiently, and abundantly. An ideal host cell for such an expression system would be able to efficiently utilize a carbon source for the production of a target polypeptide, quickly grow to high cell densities in a fermentation reaction, express the target polypeptide only when induced, and grow on a medium that is devoid of regulatory and environmental concerns. There are many hurdles to the creation of a superior host cell. First, in order to produce a recombinant polypeptide, an expression vector encoding the target protein should be inserted into the host cell. Many bacteria are capable of reverting back into an untransformed state, wherein the expression vector is eliminated from the host. Such revertants can decrease the fermentation efficiency of the production of the desired recombinant polypeptide.

Fiber-optic probes can be used to determine cell concentration measurements in the fermentation process. These determinations are often performed off-line via an optical density analyzer, for example, a visible light spectrophotometer. On-line and in situ probes are available but they frequently require calibration processes specific for each fermentation process. One probe that can be used in this manner is the fiber-optic probe of U.S. Pat. No. 4,707,134 (the Mini-View suspended solids gauge from Guided Wave, Inc., Rancho Cordova, Calif. (formerly Optical Solution Inc.)). This probe can be used for in situ detection and measurement of the intensity of light scattered by particles suspended in a transparent or translucent fluid medium. However, when the effective optical density of the medium exceeds about 50, the response can flatten out. Some mediums in need of analysis, such as biological growth media containing bacteria, can have a turbidity expressed in terms of optical density in the range of from about 50 to even as high as 200. Thus, it could be advantageous if a fiber-optic probe system were discovered that produced a more linear response in the optical density range of from about 50 to about 200.

SUMMARY OF THE INVENTION

The present invention includes methods that can be used to monitor biological systems. Furthermore, the present invention also includes methods for monitoring dynamic biological systems in a biological reactor containing developing culture fluid media. The monitoring of such a biological system can include directing light into the fluid media by way of one or more optical fibers to produce an illuminated fluid media and then measuring the intensity of light reflected from the illuminated fluid media by way of one or more optical fibers, the optical fibers being partitioned from the fluid media by a transparent window having inner and outer surfaces; the fibers having ends terminating adjacent to and confronting the inner surface of the window and extending in a direction away from the window, the corresponding ends of the fibers being radially and circumferentially spaced from one another, the corresponding ends of the fibers having converging and intersecting longitudinal projections therefrom, the intersecting longitudinal projections from the fibers being entirely within the window.

Embodiments of the present invention can also include methods for monitoring the media fermentation process by directing light into fluid media by way of one or more optical fibers to produce an illuminated fluid media and then measuring the intensity of light reflected from the illuminated fluid media by way of one or more optical fibers. Within such embodiments, the optical fibers can be partitioned from the fluid media by a transparent window having inner and outer surfaces. Additionally, the fibers can have ends terminating adjacent to and confronting the inner surface of the window and extending in a direction away from the window wherein the corresponding ends of the fibers can be radially and circumferentially spaced from one another and can have converging and intersecting longitudinal projections therefrom. Additionally, the intersecting longitudinal projections from the fibers can be entirely within the window.

In additional embodiments, the present invention can be a fiber-optic probe. The fiber-optic probe can include a housing along with a transparent window closing one end of the housing, wherein the window has inner and outer surfaces. Embodiments can also include at least two elongate optical fibers terminating within the housing, wherein the fiber can have their corresponding ends terminating adjacent to and confronting the inner surface of the window and extending in a direction away from the window through and outwardly of the housing. Additionally, the corresponding ends of the fibers can be radially and circumferentially spaced from one another and can have converging and intersecting longitudinal projections therefrom. Additionally, the cylindrical longitudinal projections from the fibers can intersect entirely within the window.

In additional embodiments, the fiber-optic probe can be used to monitor a fermentation process. The process can be for a bacterial, yeast or mammalian cell culture which can be grown in any media. The bacterial, yeast or mammalian cell culture can be ministering in situ by the fiber-optic probe and the feed and/or oxygen concentrations can be adjusted depending on the growth determination.

DETAILED DESCRIPTION OF THE INVENTION

Figure 1:
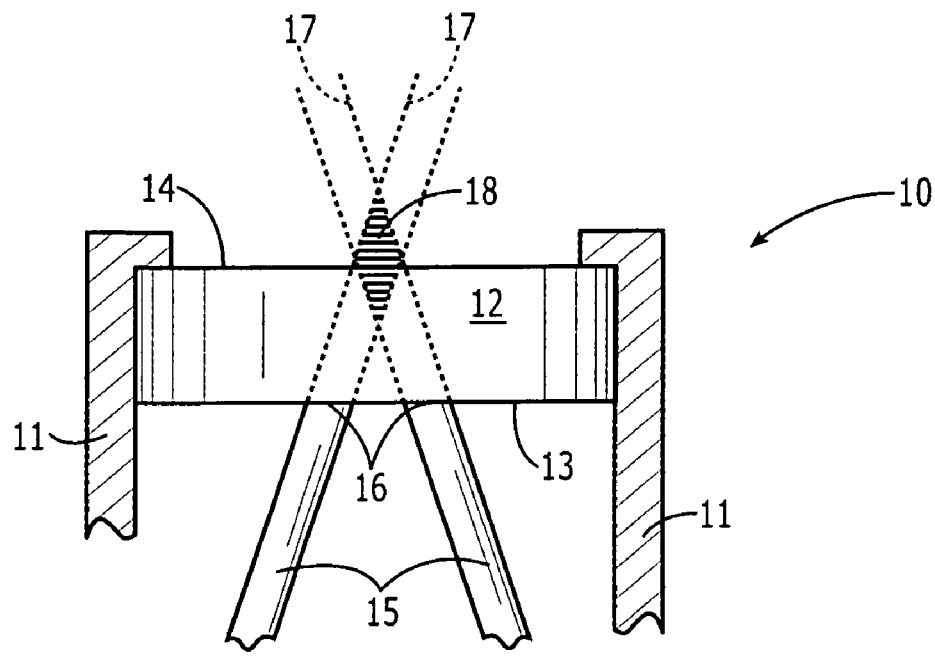
FIG. 1 is a side view, part in cross-section and part in full, of a prior art fiber-optic probe.

Biomass measurement during microbial fermentation is routine for monitoring culture performance and frequently used to trigger any required shift in the process, for example, nutrient feeds or actuation of product formation.

As used herein, the term "fermentation" includes both embodiments in which literal fermentation is employed and embodiments in which other, non-fermentative culture modes are employed. Fermentation may be performed at any scale. In one embodiment, the fermentation medium may be selected from among rich media, minimal media, and/or a mineral salts media. A rich medium may be used, but is preferably avoided. In another embodiment, either a minimal medium and/or a mineral salts medium is selected. In still another embodiment, a minimal medium is selected. In yet another embodiment, a mineral salts medium is selected. The fermentation process of the invention can be carried out in any type of fermenter.

Prior to transformation of the host cell with a nucleic acid construct encoding a prototrophic enabling enzyme, the host cell can be maintained in a media comprising a supplemental metabolite, and/or an analogue thereof, that complements the auxotrophy. Following transformation, the host cell can be grown in a media that is lacking the complementary metabolite that the host cell is auxotrophic for. In this way, host cells that do not contain the selection marker enabling prototrophy can be selected against. Likewise, cells expressing recombinant proteins from expression vectors containing an antibiotic resistance selection marker gene can be maintained prior to transformation on a medium lacking the associated antibiotic used for selection. After transformation and during the fermentation, an antibiotic can be added to the medium, at concentrations known in the art, to select against non-transformed and revertant cells.

Mineral salts media consists of mineral salts and a carbon source. A variety of carbon sources are suitable in the present invention and include, but are not limited to, materials (such as succinate, lactate, acetate, ethanol, glycerol), monosaccharides (such as glucose and fructose), oligosaccharides (such as lactose or sucrose), polysaccharides (such as starch or cellulose), or mixtures thereof, and unpurified mixtures from renewable feedstocks (such as cheese whey permeate, corn-steep liquor, sugar beet molasses, and barley malt). Examples of mineral salts media include, e.g., M9 medium, *Pseudomonas* medium (ATCC 179), and/or Davis and Mingioli medium (see, B. D. Davis and E. S. Mingioli, in *J. Bact.* 60:17-28 (1950)). The mineral salts used to make mineral salts media include those selected from among, e.g., potassium phosphates, ammonium sulfate or chloride, magnesium sulfate or chloride, and trace minerals such as calcium chloride, and borate, and/or sulfates of iron, copper, manganese, and/or zinc. No organic nitrogen source, such as peptone, tryptone, amino acids, or a yeast extract, is included in a mineral salts medium. Instead, an inorganic nitrogen source is used and this may be selected from among, e.g., ammonium salts, aqueous ammonia, and gaseous ammonia. A particular mineral salts medium will contain, for example, glucose and/or glycerol as the carbon source. In comparison to mineral salts media, minimal media can also contain mineral salts and a carbon source, but can be supplemented with, e.g., low levels of amino acids, vitamins, peptones, or other ingredients, though these are added at very minimal levels.

The probe of the present invention can utilize any fermentation format. Examples of formats that may be employed herein include batch, fed-batch, semi-continuous, and continuous fermentation modes.

A classical batch fermentation is a closed system where the composition of the medium is set at the beginning of the fermentation and not subjected to artificial alterations during the fermentation. Thus, at the beginning of the fermentation, the medium is inoculated with the desired organism or organisms and fermentation is permitted to occur adding nothing to the system. Typically, however, a batch fermentation is "batch" with respect to the addition of carbon source and attempts are often made at controlling factors such as pH and oxygen concentration. In batch systems, the metabolite and biomass compositions of the system change constantly up to the time the fermentation is stopped. Within batch cultures, cells moderate through a static lag phase to a high growth log phase and finally to a stationary phase where growth rate is diminished or halted. If untreated, cells in the stationary phase will eventually die.

A variation on the standard batch system is the fed-batch system. Fed-batch fermentation processes are also suitable in the present invention and comprise a typical batch system with the exception that the substrate is added in increments as the fermentation progresses. Fed-batch systems are useful when catabolite repression is apt to inhibit the metabolism of the cells and where it is desirable to have limited amounts of substrate in the medium. Using a fed-batch system, it can be possible to maintain a steady concentration of substrate at non-toxic levels while accommodating maximum bioconversion of the substrate to product.

Batch and fed-batch fermentations are known in the art and examples may be found in, for example, Thomas D. Brock, in *Biotechnology: A Textbook of Industrial Microbiology,* 2nd ed.; Sinauer Associates, Inc.: Sunderland, Mass., 1989; or Mukund V. Deshpande, *Appl. Biochem. Biotechnol.* 36:227 (1992).

It is contemplated that the method would be adaptable to semi-continuous and continuous fermentation methods. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen source at low concentration and allow all other parameters to be in excess. In other systems, a number of factors affecting growth can be altered continuously while the cell concentration, measured by medium turbidity, is kept constant. Continuous systems strive to maintain steady state growth conditions and, thus, the cell loss due to medium being drawn off must be balanced against the cell growth rate in the fermentation. Methods of modulating nutrients and growth factors for continuous fermentation processes, as well as techniques for maximizing the rate of product formation, are well known in the art of industrial microbiology and a variety of methods are detailed by Brock, supra.

It is contemplated that the present invention may be practiced using either batch, fed-batch, semi-continuous or continuous processes and that any known mode of fermentation would be suitable.

Any scale (i.e., volume) of fermentation may be used. Thus, e.g., microliter-scale, centiliter-scale, and deciliter-scale fermentation volumes may be used; and 1 Liter scale and larger fermentation volumes can be used. In one embodiment, the fermentation volume will be at or above 1 Liter. In another embodiment, the fermentation volume will be at or above 5 Liters, 10 Liters, 15 Liters, 20 Liters, 25 Liters, 50 Liters, 75 Liters, 100 Liters, 200 Liters, 500 Liters, 1,000 Liters, 2,000 Liters, 5,000 Liters, 10,000 Liters or 50,000 Liters.

Culture performance is commonly determined by off-line methods such as absorbance with a laboratory spectrophotometer. Typically, the production of a desired biopharmaceutical by the bacteria in the bioreactor is preceded by a bacteria growth phase in which the cell density of the bacteria is increased to increase the amount of biopharmaceutical produced during the later production phase. The cell density at the end of the growth phase can easily exceed 100 optical density units. Optimum control of such fermentation systems requires the determination of cell density throughout the growth and production phases. Bacteria that can be used with this system include, but are not limited to, *Pseudomonas, E. coli, Streptococcus, Streptomyces, Staphylococcus, Acetobacter, Arthrobacter, Bacillus*, etc., organisms. *Pseudomonas* sp. may include, but are not limited to, *Pseudomonas putida, Pseudomonas fluorescens, Pseudomonas aeruginosa* and *Pseudomonas mendocina*. This system can also be used by a yeast expression system, such as *Saccharomyces cerevisiae* and *Pichia pastoris*. Additionally, the probe can be used for monitoring fermentation in a mammalian culture system. This system can monitor and control the feeding of *E. coli* fermentations that are very sensitive to overfeeding of glucose. Examples of the difficulties of monitoring and controlling the feeding of *E. coli* are exemplified and described by Yamane, 1993 (*Biotechnol. Prog.* 9:81-85).

Prior art methods for the measurement of cell density in excess of 100 optical density units typically require sampling of the growth media out from the reactor, followed by diluting of the sample (typically a 1:1000 dilution), determining the optical density of the diluted sample, and finally calculating the optical density of the undiluted sample. Such prior art methods can have a number of problems such as the logistics of obtaining the samples, the risk of biological contamination of the bioreactor, the risk of otherwise disturbing the process, and the time lapse between taking a sample and obtaining a result, during which time lapse, control of the system might be compromised. In addition, the accuracy of the prior art method of diluting a sample followed by optical density measurement tended to be poor. In a collaborative study of the prior art method between four analysts at different laboratories on a single sample, average results from each laboratory varied over a range of 23 optical density units and about 40 percent of the results were outside of plus or minus 5 optical density units from the mean result.

Various in situ biomass or cell density probes based on fiber optics or capacitance have also been described. For example, Wu et al. in *Biotechnology and Bioengineering* (1995) 45:495-502, evaluated six commercially available probes for the linearity of the probe responses in correlation to cell numbers in murine hybridoma fermentations with mixed results. The Aquasant and INGOLD™ backscattering probes produced the most linear responses. Hatch and Veilleux in *Biotechnology and Bioengineering* (1995) 46:371-374, reported the use of an optical density probe to monitor yeast fermentations on-line. Another class of in situ biomass probes based on capacitance or permittivity measurements have also been reported (EP1138758A1; WO0179828A1). These probes can be variable in performance and result in a non-linear response over a wide range of biomass, for example, from 1 g/L to 100 g/L dry cell weight or 2 to 200 absorbance units at 600 nm.

Embodiments of the present invention can include real time in situ determination of cell concentration measurements in a bioreactor over a very wide range. In terms of optical density, the method and apparatus of the instant invention can provide accurate and reproducible data at relatively low optical densities, as well as at relatively high optical densities in excess of 100 optical density units. The embodiments of the present invention can also allow for the optical density results obtained from fermentation cultures in vigorously aerated and agitated bioreactors without being subject to interference by agitation rate or the presence in the fluid media of gas bubbles. The embodiments of the present invention can also allow for the fiber-optic probe to be sterilized in place.

Embodiments of the invention also include methods for real-time monitoring of a dynamic biological system in a biological reactor containing developing culture fluid media. Such embodiments include an in situ biomass analyzer, such as an in situ optical probe, to allow for the precise feeding of nutrients to fed-batch high density recombinant fermentations. Such fermentations can include *Pseudomonas* or *Escherichia coli* fermentations. Generally, *E. coli* are particularly sensitive to overfeeding. Cultures that are overfed will produce acetic acid that can accumulate to toxic levels and prevent further growth and result in loss of productivity. Under-feeding can slow the growth and affect productivity as well. The in situ biomass probe can allow for a continuous and a more direct method for determining the appropriate feed rates with minimum operator intervention. The in situ probe can reduce variability and ensure that the correct feed rates are delivered to the culture.

Embodiments of the present invention also include methods for directing light into the fluid media by way of one or more optical fibers to produce an illuminated fluid media and then measuring the intensity of light reflected from the illuminated fluid media by way of one or more optical fibers. The optical fibers can be partitioned from the fluid media by a transparent window having inner and outer surfaces. The optical fibers can have ends terminating adjacent to and confronting the inner surface of the window and extending in a direction away from the window. Additionally, the corresponding ends of the optical fibers can be radially and circumferentially spaced from one another and have converging and intersecting longitudinal projections therefrom, wherein the intersecting longitudinal projections from the fibers can be entirely within the window. The methods and apparatuses of the present invention can be used to determine the turbidity of any fluid media.

Embodiments of the present invention can also include a probe that can be used in high sludge outfalls to measure solids concentration in waste water treatment processes. Certain latex formulations containing high solids loading could also be measured to advantageously control the final product specification.

Embodiments of the present invention also include a fiber-optic biomass probe that can provide a feedback loop to detect any adjustments to the biomass and growth rate of the culture throughout cultivation. This frequent feedback biomass information can provide a significant improvement to the exponential feed program by ensuring timely adjustments to the feed rates in response to any changes in the culture growth rate. The biomass probe can allow for frequent calculation of the actual growth rates of the culture, enabling frequent adjustments of the substrate feed rates to ensure substrate limitation. For example, an improved exponential substrate feed program employing the fiber-optic biomass probe can be described by:

$$F_{t_2} = \frac{\mu_{t_2} X_{t_1} V_{t_1} e^{\mu_{t_2}(t_2 - t_1)}}{Y_{x/s} S_0}$$

where, at a given time $t_2$ in h, $F_{t_2}$ is the substrate feed flow rate in L/h, $\mu_{t_2}$ is the specific growth rate in 1/h, $X_{t_1}$ and $V_{t_1}$ are the biomass in g and the volume of the culture in L at a previous time point of $t_1$, $Y_{x/s}$ is the yield coefficient of the biomass on the limiting substrate in g/g and $S_0$ is the substrate concentration in the feed in g/L. The initial volume of the culture, $V_{t_1}$, can either be calculated by a summation of the totalized feed volume with the previous calculated volume or directly determined by a fermentor volume detector. $X_1$ and $X_{t_2}$ can be determined by the fiber-optic biomass probe and used to calculate the growth rate at time $t_2$, $\mu t_2$, using the following equation:

$$\mu_{t_2} = \frac{Ln X_{t_2} - Ln X_{t_1}}{t_2 - t_1}$$

The biomass probe can thus ensure timely adjustments to the substrate feed rate in response to any changes to the growth of the culture, avoiding overfeeding in occasions where the culture growth slows, for example, when the culture becomes oxygen limited.

Referring now to FIG. 1, therein is shown a side view of a fiber-optic probe 10 according to the teachings of U.S. Pat. No. 4,707,134 (hereinafter "the '134 Patent"), herein fully incorporated by reference. Reference to U.S. Pat. No. 4,909,588 should be made to understand the details of construction (such as seals, spacers and window materials), as well as the details of operation (such as light sources and detectors) of fiber-optic probes used to measure turbidity. The probe 10 comprises a housing 11, a transparent window 12 closing one end of the housing 11 and having inner surface 13 and outer surface 14. The probe 10 contains two elongate optical fibers 15 within the housing 11, the fibers 15 having their corresponding ends 16 terminating adjacent to and confronting the inner surface 13 of the window 12 and extending in a direction away from the window 12 and outwardly through the housing 11, the corresponding ends 16 of the fibers 15 being radially and circumferentially spaced from one another.

Referring still to FIG. 1, the ends 16 of the fibers 15 have converging and longitudinal cylindrical projections 17 therefrom. The projections 17 intersect in the intersecting volume 18, which is partially within the window 12 and partially outside the window 12. Such an arrangement is preferred in the prior art in those instances in which the concentration of particles in the sample is relatively high, see column 4, line 65, to column 5, line 5, of the '134 Patent.

Figure 2:
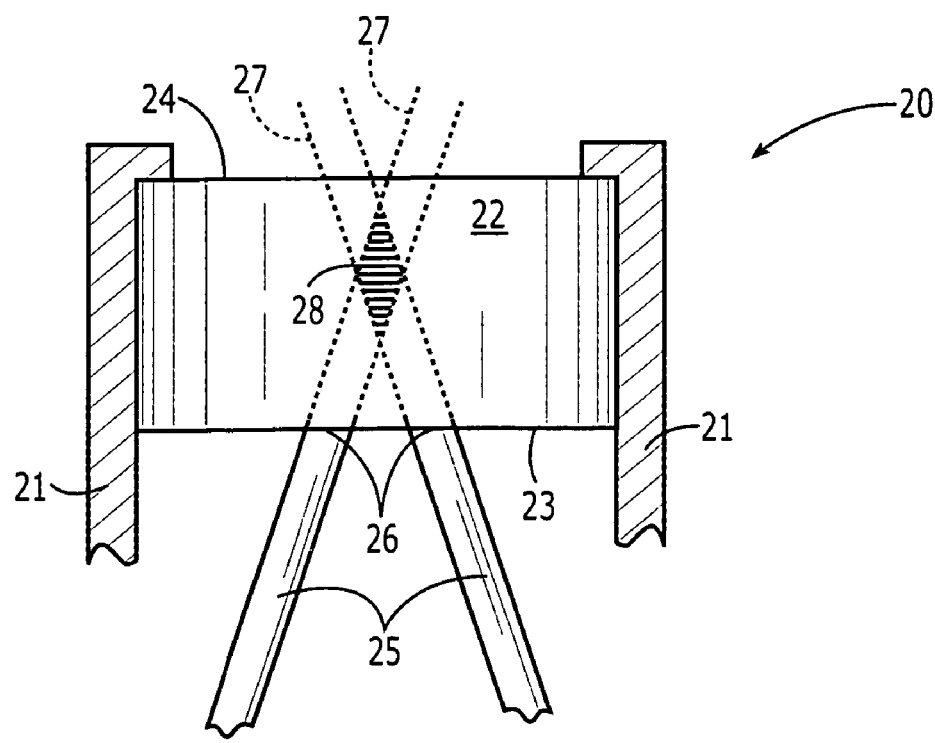
FIG. 2 is a side view, part in cross-section and part in full, of a fiber-optic probe of the instant invention.

Referring now to FIG. 2, therein is shown a side view, part in cross-section and part in full, of a fiber-optic probe 20 of the instant invention. The probe 20 comprises a housing 21, a transparent window 22 closing one end of the housing 21 and having inner surface 23 and outer surface 24. The probe 20 contains two elongate optical fibers 25 within the housing 21, the fibers 25 having their corresponding ends 26 terminating adjacent to and confronting the inner surface 23 of the window 22 and extending in a direction away from the window 22 through and outwardly of the housing 21, the corresponding ends 26 of the fibers 25 being radially and circumferentially spaced from one another. The ends 26 of the fibers 25 have converging and longitudinal projections 27 therefrom. The projections 27 intersect in the intersecting volume 28, which is entirely within the window 22.

Figure 3:
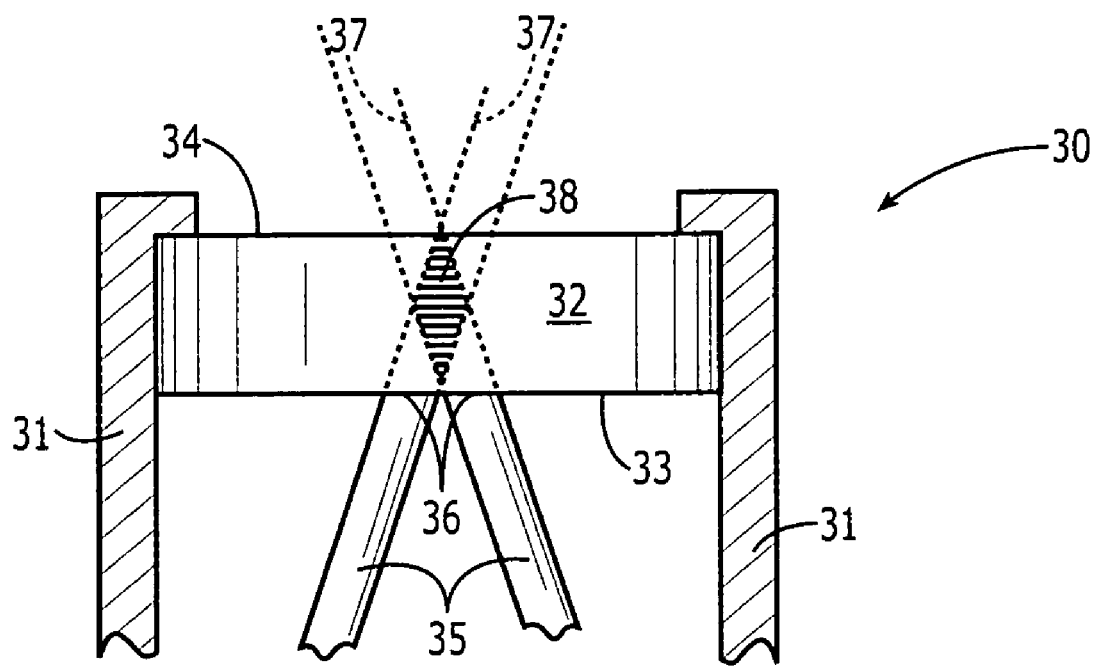
FIG. 3 is a side view, part in cross-section and part in full, of another fiber-optic probe of the instant invention.

Referring now to FIG. 3, therein is shown a side view, part in cross-section and part in full, of a preferred fiber-optic probe 30 of the instant invention. The probe 30 comprises a housing 31, a transparent window 32 closing one end of the housing 31, and having inner surface 33 and outer surface 34. The probe 30 contains two elongate optical fibers 35 within the housing 31, the fibers 35 having their corresponding ends 36 terminating adjacent to and confronting the inner surface 33 of the window 32 and extending in a direction away from the window 32 through and outwardly of the housing 31, the corresponding ends 36 of the fibers 35 being radially and circumferentially spaced from one another. The ends 36 of the fibers 35 have converging and longitudinal projections 37 therefrom. The projections 37 intersect in the intersecting volume 38, which is entirely within the window 32. It will be noted that in the probe 30, the spacing between the ends 36 of the fibers 35 is minimal and the angle of intersection of the longitudinal axis of the housing 31 and the longitudinal projection 37 from each optical fiber 35 is about twenty degrees. Although such an angle of about twenty degrees is highly preferred, it should be understood that any angle can be used as long as the intersecting volume of the projections from the optical fibers is entirely within the window. As a general teaching, such angle can be in the range of from about ten to about thirty degrees.

Figure 4:
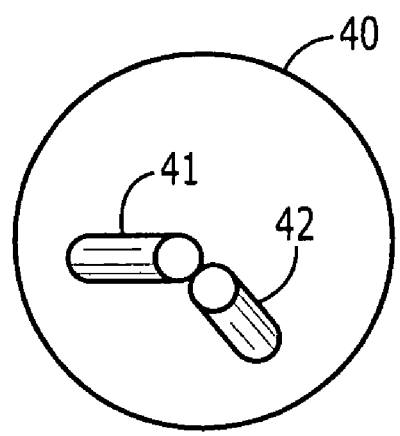
FIG. 4 is a top view of the window and underlying optical fibers of a fiber-optic probe of the instant invention employing two optical fibers.

Referring now to FIG. 4, therein is shown a top view of the window 40 and underlying optical fibers of a preferred fiber-optic probe of the instant invention employing a first optical fiber 41 and a second optical fiber 42. In use, light can be directed through the first optical fiber 41 while the second optical fiber 42 can be used for light detection. It will be noted that the first optical fiber 41 is spaced radially and circumferentially from the second optical fiber 42.

Figure 5:
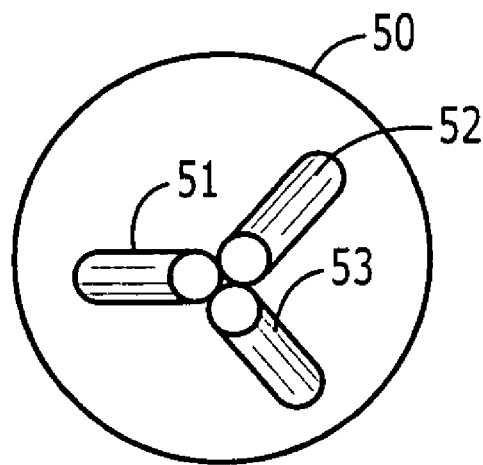
FIG. 5 is a top view of the window and underlying optical fibers of a fiber-optic probe of the instant invention employing three optical fibers.

Referring now to FIG. 5, therein is shown a top view of the window 50 and underlying optical fibers of a highly preferred fiber-optic probe of the instant invention employing a first optical fiber 51, a second optical fiber 52, and a third optical fiber 53. In use, light can be directed through the first optical fiber 51, while the second optical fiber 52 can be used for light detection, while maintaining the third optical fiber 53 in reserve in case the first optical fiber 51 or the second optical fiber 52 becomes inoperable for some reason (such as a broken fiber) after extended use. It will be noted that the optical fibers 51, 52 and 53 are spaced radially and circumferentially from each other.

Figure 6:
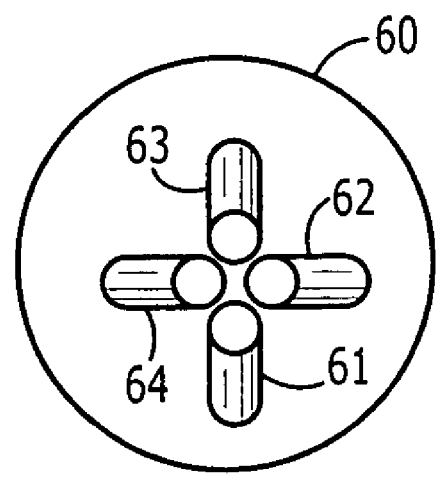
FIG. 6 is a top view of the window and underlying optical fibers of a fiber-optic probe of the instant invention employing four optical fibers.

Referring now to FIG. 6, therein is shown a top view of the window 60 and underlying optical fibers of a preferred fiber-optic probe of the instant invention employing a first optical fiber 61, a second optical fiber 62, a third optical fiber 63 and a fourth optical fiber 64. In use, light can be directed through the first optical fiber 61, while the second optical fiber 62 can be used for light detection, while maintaining the third and fourth optical fiber 63 and 64 in reserve in case the first optical fiber 61 or the second optical fiber 62 becomes inoperable after extended use. Alternatively, of course, light can be directed through the first and third optical fibers 61 and 63 while the second and fourth optical fibers 62 and 64 are used for light detection. It will be noted that the optical fibers 61, 62, 63 and 64 are spaced radially and circumferentially from each other.

In order that this invention may be better understood, the following examples are set forth. These examples are for purposes of illustration only, and are not to be construed as limiting the scope of the invention in any manner.

Example 1

A fiber-optic probe is assembled according to the specific teachings above and otherwise according to the teachings of U.S. Pat. No. 4,909,588. The window of the probe is made of sapphire and is stepped as shown in FIG. 2 of the '588 patent. The window is two millimeters thick. The gaskets sealing the window to the tubular stainless steel housing of the probe are made of KALREZ™ brand type 6375 elastomer. The probe contains three 0.020-inch diameter optical fibers as shown in FIG. 5. The angle of intersection of the longitudinal axis of the housing of the probe and the longitudinal projection from each optical fiber is about twenty degrees.

Figure 7:
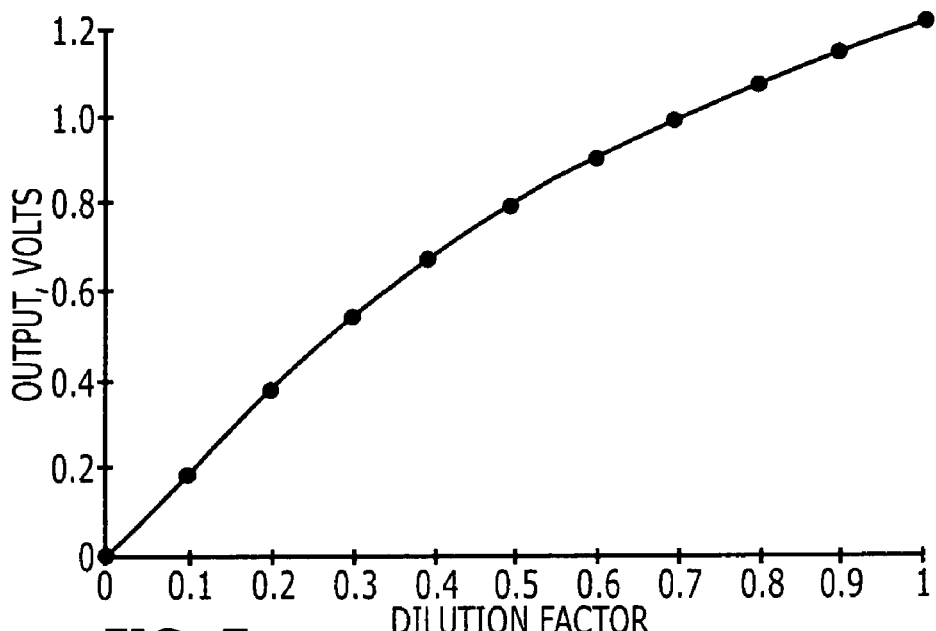
FIG. 7 is a plot of response v. turbidity using a fiber-optic probe of the instant invention.

The prior art fiber-optic probe of a MiniView™ brand suspended solids gauge from Guided Wave, Inc. (Rancho Cordova, Calif.) (formerly Optical Solutions, Inc. (Roseville, Calif.)), is replaced with the fiber-optic probe of the preceding paragraph. A series of turbidity standards are prepared using GFS Chemicals (Powell, Ohio) 0.121-micrometer diameter styrene divinyl benzene copolymer beads in water having a turbidity of 120,000 NTU is diluted in the range of from 0.9× to 0.1×. These standards are analyzed using the MiniView™ suspended solids gauge and the fiber-optic probe of the preceding paragraph to produce the response v. dilution factor data shown in FIG. 7.

Example 2

Figure 8:
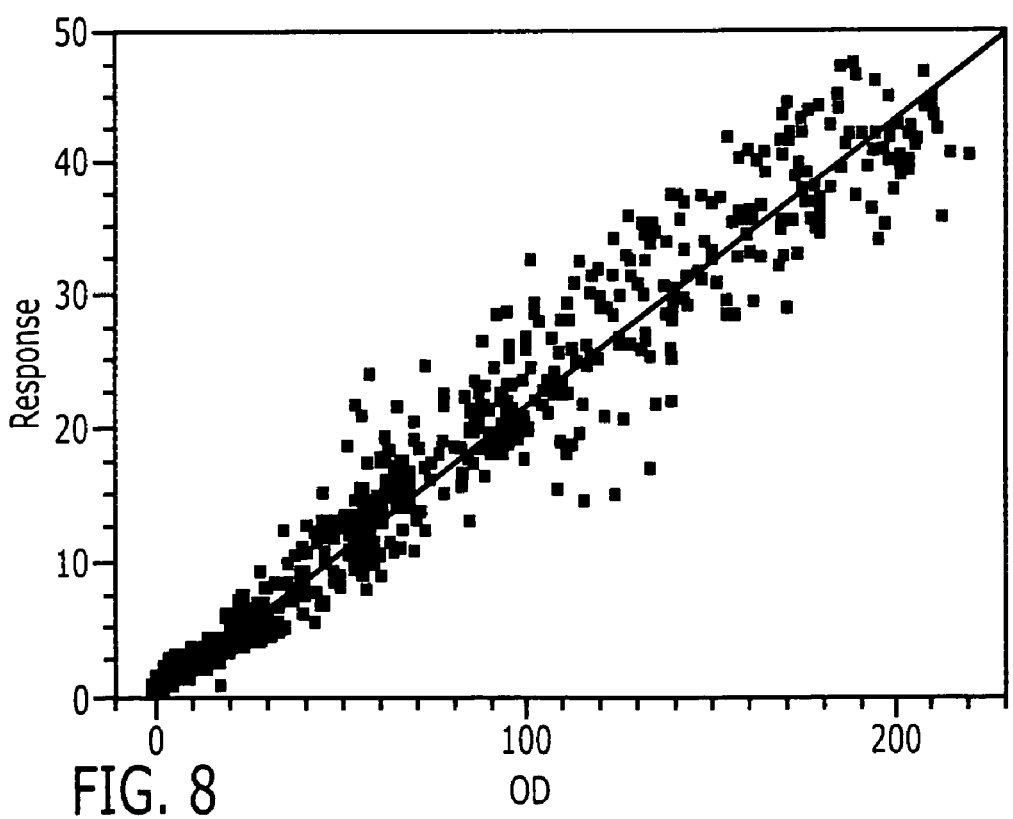
FIG. 8 is a correlation plot comparing results obtained from 89 fermentation runs, representing a total of four strains of *Pseudomonas* bacteria, using the method of the instant invention and an off-line method for determining the turbidity of biomass in a 20-liter bioreactor.

Referring now to FIG. 8, therein is shown a correlation plot of the response of the probe system of the instant invention used to determine the turbidity of cell growth *Pseudomonas* biomass on-line in the bioreactor v. data obtained for the same material by the prior art method of taking a sample of the cell growth biomass from the bioreactor, diluting the sample and then determining the optical density (OD) of the sample. The data represent the compilation of 89 separate fermentations, spanning both growth and production phases, using four independent *Pseudomonas* strains in 20-liter bioreactors, which demonstrates the high consistency of the probe to ODs of up to and greater than 200, or 100 g/L dry cell weight.

Example 3

Figure 9:
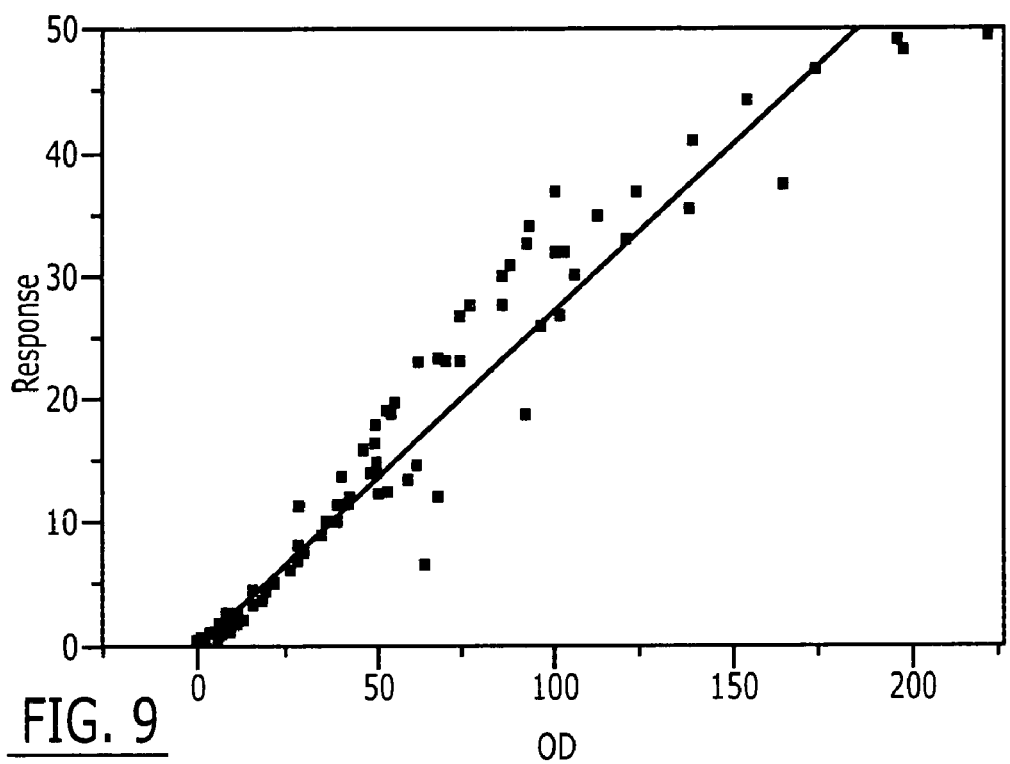
FIG. 9 is a correlation plot comparing results obtained using the method of the instant invention and an off-line method for determining the turbidity of *E. coli* biomass in a 20-liter bioreactor.

A bioreactor containing *E. coli* in a liquid media is cycled through its growth and production phases. Referring now to FIG. 9, therein is shown a correlation plot of the response of the probe system of the instant invention used to determine the turbidity of cell growth *E. coli* biomass on-line in the bioreactor v. data obtained for the same material by the prior art method of taking a sample of the cell growth biomass from the bioreactor, diluting the sample and then determining the optical density (OD) of the sample. The data in FIG. 9, which correspond to a compilation of seven independent fermentation experiments, show the excellent correlation between the system using the probe of the instant invention and the prior art method.

Example 4

Figure 10:
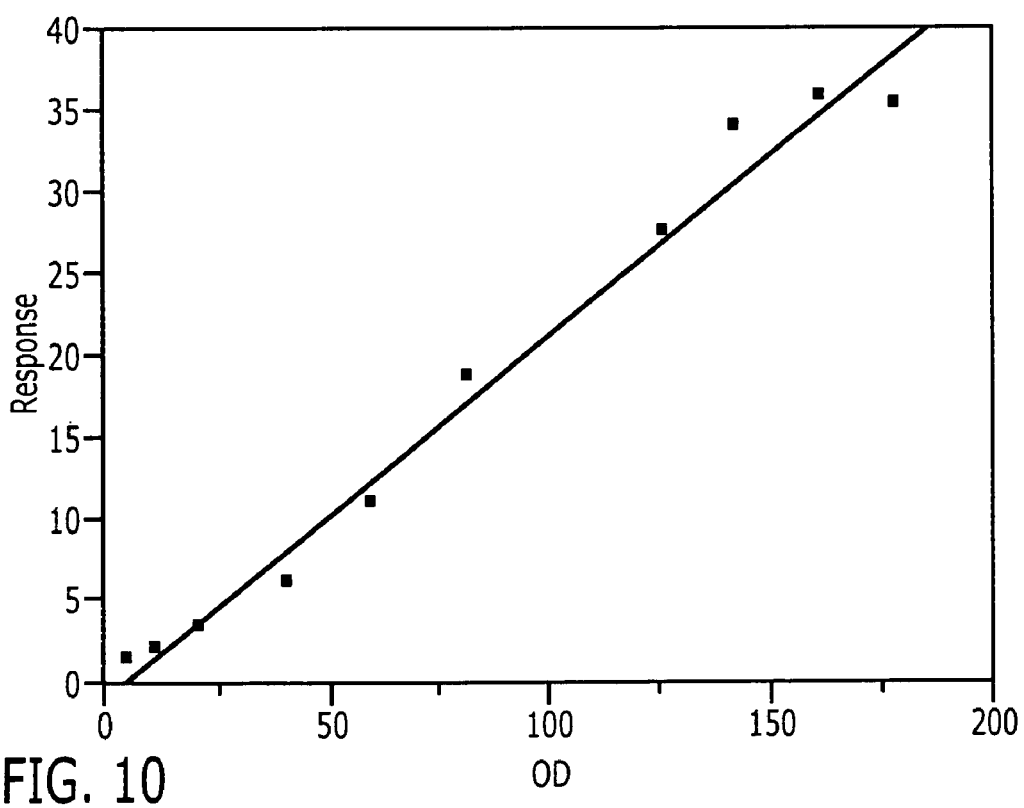
FIG. 10 is a correlation plot comparing results obtained using the method of the instant invention and an off-line method for determining the turbidity of *Pseudomonas* biomass during fermentation in a 1500-liter bioreactor.

A 1500-liter bioreactor containing *Pseudomonas* in a liquid media is cycled through its growth and production phase. Referring now to FIG. 10, therein is shown a correlation plot of the response of the probe system of the instant invention used to determine the turbidity of cell growth or *Pseudomonas* biomass on-line in the bioreactor v. data obtained for the same material by the prior art method of taking a sample of the cell growth biomass from the bioreactor, diluting the sample and then determining the optical density (OD) of the sample.

Example 5

The good correlation between the fiber-optic probe and the actual biomass of different bacterial species and at different scales demonstrated in Examples 2, 3 and 4 makes it a particularly suitable tool to control carbon feed rates in fed-batch fermentation cultures where it is essential for growth to be limited by the carbon source. As reviewed by L. Yee and H. W. Blanch in Biotechnology (1992) 10:1550-1556, excess glucose can cause accumulation of inhibitory metabolic by-products such as acetate in fed-batch *E. coli* fermentations that can be detrimental to cell growth and recombinant protein expression. Similarly, excessive carbon feeding can cause accumulation of ethanol in recombinant yeast fermentations even under aerobic conditions. Several approaches to ensure limiting substrate feeding have been reported. For example, D. W. Zabriskie, D. A. Wareheim and M. J. Polansky in *Journal of Industrial Microbiology* (1987) 2:87-95, and L. Yee and H. W. Blanch in *Biotechnology* (1992) 10:1550-1556, described an exponential feeding profile by using the equation:

$$F = \frac{\mu X_0 V_0 e^{\mu t}}{Y_{x/s} S_0}$$

where F is the substrate feed flow rate in L/h, $\mu$ is the specific growth rate in 1/h, $X_0$ is the initial biomass in g, $V_0$ is the initial volume in L, t is the time in h, $Y_{x/s}$ is the yield coefficient of the biomass on the limiting substrate in g/g and $S_0$ is the substrate concentration in the feed in g/L. In this instance, for a substrate to be limiting, the specific growth rate used in the equation has to be less than the maximum growth rate of the culture and the other factors, such as initial biomass, volumes and yield coefficients, have to be accurate. Another assumption is that the culture is in the exponential growth phase. If any of the factors or assumptions are wrong, for example, the initial biomass in the culture is miscalculated or the culture is in lag phase or not growing exponentially, the substrate feed rate can be overestimated, resulting in overfeeding of the substrate, followed by accumulation of inhibitory metabolites. The fiber-optic biomass probe of Examples 2, 3 and 4 provides a feedback loop to detect any adjustments to the biomass and growth rate of the culture throughout cultivation.

While the instant invention has been described above according to its preferred embodiments, it can be modified within the spirit and scope of this disclosure. This application is, therefore, intended to cover any variations, uses, or adaptations of the instant invention using the general principles disclosed herein. Further, the instant application is intended to cover such departures from the present disclosure as come within the known or customary practice in the art to which this invention pertains and which fall within the limits of the following claims.

What is claimed is:

1. A method for monitoring a bacterial system comprising:
    directing light into fluid media by way of one or more optical fibers to produce an illuminated fluid media; and measuring the intensity of light reflected from the illuminated fluid media by way of one or more optical fibers, the one or more optical fibers being partitioned from the illuminated fluid media by a transparent window having inner and outer surfaces, the one or more optical fibers having ends terminating adjacent to and confronting the inner surface of the window and extending in a direction away from the window, corresponding ends of the one or more optical fibers being radially and circumferentially spaced from one another and having converging and intersecting longitudinal projections therefrom, the intersecting volume of the longitudinal projections from the optical fibers being entirely within the window.

2. The method according to claim 1, wherein an angle of intersection of the longitudinal projections from the optical fibers is in a range of from about ten to about thirty degrees.

3. The method according to claim 1, wherein the bacterial system is a fluid media.

4. The method according to claim 3, further comprising the step of adding glucose or glycerol to the fluid media at a rate determined by a turbidity determination.

5. The method according to claim 4, wherein the turbidity determination is not interfered with by an agitation rate of the fluid media or by bubbles of gas contained in the fluid media.

6. The method according to claim 1, wherein the bacteria is selected from the group consisting of *Pseudomonas* sp. or *E. coli* cells.

7. A fiber-optic probe, comprising:
    a housing;
    a transparent window closing one end of the housing, the window having inner and outer surfaces; and
    at least two elongate optical fibers terminating within the housing, the at least two elongate optical fibers having their corresponding ends terminating adjacent to and confronting the inner surface of the window and extending in a direction away from the window through and outwardly of the housing, the corresponding ends of the fibers being radially and circumferentially spaced from one another, the corresponding ends of the fibers having converging and intersecting longitudinal projections therefrom, the volume of the cylindrical longitudinal projections from the fibers intersecting entirely within the window.

8. The fiber-optic probe of claim 7, wherein the housing is tubular in shape, the intersecting longitudinal projections from the optical fibers intersecting essentially on the longitudinal axis of the housing, the angle of intersection of the longitudinal axis of the housing and the longitudinal projection from each optical fiber being in the range of from about ten to about thirty degrees.

9. The fiber-optic probe of claim 8, containing three optical fibers, the intersecting longitudinal projections from the optical fibers intersecting essentially on the longitudinal axis of the housing, the angle of intersection of the longitudinal axis of the housing and the longitudinal projection from each optical fiber being about twenty degrees, the ends of each optical fiber terminating adjacent to and confronting the inner surface of the window being essentially equally circumferentially spaced from each other.

10. A method for monitoring a fermentation process comprising:
    providing the fiber-optic probe of claim 7;
    providing a bacterial, yeast or mammalian cell culture;
    growing said bacterial, yeast or mammalian cell culture in a media;
    determining the growth of the bacterial, yeast or mammalian cell culture in situ by the fiber-optic probe; and
    adjusting feed and/or oxygen concentrations on the basis of the growth determination.

11. A method for monitoring culture performance comprising:
    directing light into a fluid media by way of one or more optical fibers to produce an illuminated fluid media;
    measuring the intensity of light reflected from the illuminated fluid media by way of one or more optical fibers, the optical fibers being partitioned from the fluid media by a transparent window having inner and outer surfaces, the optical fibers having ends terminating adjacent to and confronting the inner surface of the window and extending in a direction away from the window, the corresponding ends of the optical fibers being radially and circumferentially spaced from one another, the corresponding ends of the optical fibers having converging and intersecting longitudinal projections therefrom, the intersecting volume of the longitudinal projections from the optical fibers being entirely within the window; and
    analyzing said intensity of light to determine the culture performance.

12. The method according to claim 11, wherein the method of monitoring culture performance occurs during a fermentation process.

13. The method according to claim 11, wherein the method of monitoring culture performance is performed in situ.

14. The method according to claim 11, wherein a culture measured within the culture performance is selected from the group consisting of bacterial, yeast and mammalian cells.

15. The method according to claim 14, further comprising determining the optical density of the bacterial cells.

16. The method according to claim 14, wherein the bacterial cells are selected from the group consisting of *Pseudomonas* sp. or *E. Coli* cells.

17. The method according to claim 14, further comprising analyzing the oxygen rate of the bacterial cells.

18. The method according to claim 11, further comprising determining the turbidity of cell growth.

19. The method according to claim 11, wherein said method for monitoring culture performance comprises measuring cell concentration.

20. The method according to claim 11, further comprising analyzing the growth rate of the cell concentration and adjusting a substrate feed rate based upon changes in the growth rate.

* * * * *